United States Patent
Loick et al.

(10) Patent No.: US 10,738,141 B2
(45) Date of Patent: *Aug. 11, 2020

(54) SUPERABSORBENT POLYMERS WITH IMPROVED ODOR CONTROL CAPACITY AND PROCESS FOR THE PRODUCTION THEREOF

(71) Applicant: EVONIK OPERATIONS GMBH, Essen (DE)

(72) Inventors: Christoph Loick, Duisburg (DE); Scott Smith, Düsseldorf (DE)

(73) Assignee: Evonik Operations GmbH, Essen (DE)

(*) Notice: Subject to any disclaimer, the term of this patent is extended or adjusted under 35 U.S.C. 154(b) by 0 days.

This patent is subject to a terminal disclaimer.

(21) Appl. No.: 16/394,881

(22) Filed: Apr. 25, 2019

(65) Prior Publication Data
US 2019/0248939 A1    Aug. 15, 2019

Related U.S. Application Data

(62) Division of application No. 14/639,177, filed on Mar. 5, 2015, now Pat. No. 10,287,379.

(60) Provisional application No. 61/948,114, filed on Mar. 5, 2014.

(51) Int. Cl.
| | | |
|---|---|---|
| A61L 15/22 | (2006.01) |
| A61L 15/46 | (2006.01) |
| C08F 220/06 | (2006.01) |
| C08J 3/24 | (2006.01) |
| A61L 15/60 | (2006.01) |
| C08J 3/075 | (2006.01) |

(52) U.S. Cl.
CPC .......... *C08F 220/06* (2013.01); *A61L 15/225* (2013.01); *A61L 15/46* (2013.01); *A61L 15/60* (2013.01); *C08J 3/075* (2013.01); *C08J 3/245* (2013.01); *A61L 2300/11* (2013.01); *A61L 2300/80* (2013.01); *C08J 2333/02* (2013.01)

(58) Field of Classification Search
CPC ...... C08F 220/06; C08J 3/245; C08J 2333/02; A61L 15/46; A61L 15/225; A61L 2300/80
See application file for complete search history.

(56) References Cited

U.S. PATENT DOCUMENTS

| | | |
|---|---|---|
| 4,076,663 A | 2/1978 | Masuda et al. |
| 4,179,367 A | 12/1979 | Barthell et al. |
| 4,286,082 A | 8/1981 | Tsubakimoto et al. |
| 4,587,308 A | 5/1986 | Makita et al. |
| 4,783,510 A | 11/1988 | Saotome |
| 5,409,771 A | 4/1995 | Dahmen et al. |
| 5,451,613 A | 9/1995 | Smith et al. |
| 5,462,972 A | 10/1995 | Smith et al. |
| 5,610,220 A | 3/1997 | Klimmek et al. |
| 5,672,633 A | 9/1997 | Brehm et al. |
| 5,712,316 A | 1/1998 | Dahmen et al. |
| 6,087,450 A | 7/2000 | Breitbach et al. |
| 6,143,821 A | 11/2000 | Houben |
| 6,605,673 B1 | 8/2003 | Mertens et al. |
| 6,620,889 B1 | 9/2003 | Mertens et al. |
| 6,623,848 B2 | 9/2003 | Brehm et al. |
| 6,906,131 B2 | 6/2005 | Ahmed et al. |
| 6,911,572 B1 | 6/2005 | Bruhn et al. |
| 6,958,429 B2 | 10/2005 | Bruhn et al. |
| 7,163,969 B2 | 1/2007 | Ahmed et al. |
| 7,169,843 B2 | 1/2007 | Smith et al. |
| 7,173,086 B2 | 2/2007 | Smith et al. |
| 7,179,862 B2 | 2/2007 | Mertens et al. |
| 7,241,820 B2 | 7/2007 | Smith et al. |
| 7,291,674 B2 | 11/2007 | Kang et al. |
| 7,312,286 B2 | 12/2007 | Lang et al. |
| 7,335,713 B2 | 2/2008 | Lang et al. |
| 7,399,813 B2 | 7/2008 | Lang et al. |
| 7,427,650 B2 | 9/2008 | Smith et al. |
| 7,482,058 B2 | 1/2009 | Ahmed et al. |
| 7,488,541 B2 | 2/2009 | Ahmed et al. |
| 7,579,402 B2 | 8/2009 | Ahmed et al. |
| 7,625,957 B2 | 12/2009 | Harren et al. |
| 7,776,984 B2 | 8/2010 | Frank |
| 7,777,093 B2 | 8/2010 | Smith et al. |
| 7,795,345 B2 | 9/2010 | Smith et al. |
| 7,812,082 B2 | 10/2010 | McIntosh et al. |
| 7,816,426 B2 | 10/2010 | Ahmed et al. |
| 7,842,386 B2 | 11/2010 | Loeker et al. |
| 7,910,688 B2 | 3/2011 | Tian et al. |
| 8,063,118 B2 | 11/2011 | Ahmed et al. |

(Continued)

FOREIGN PATENT DOCUMENTS

| | | |
|---|---|---|
| CA | 2460152 A1 | 3/2003 |
| CN | 1568347 | 1/2005 |

(Continued)

OTHER PUBLICATIONS

German language European Search Report dated Jul. 31, 2015 in EP 15 15 7114 (3 pages).

*Primary Examiner* — Irina S Zemel
*Assistant Examiner* — Jeffrey S Lenihan
(74) *Attorney, Agent, or Firm* — Linda S. Li; Jason S. Ngui

(57) ABSTRACT

The present invention relates to a water-absorbing polymer and to a process for preparation, including finishing the water-absorbing polymer, with 0.0001 to 3% by weight, of a peroxo compound, based on the acrylic acid, after the polymerization is treated, and to a process for producing a hydrogel polymer, to the product of the process and to use.

5 Claims, No Drawings

(56) References Cited

U.S. PATENT DOCUMENTS

| | | | |
|---|---|---|---|
| 8,222,477 B2 | 7/2012 | Azad et al. | |
| 8,236,876 B2 | 8/2012 | Ahmed et al. | |
| 8,236,884 B2 | 8/2012 | Smith et al. | |
| 8,288,002 B2 | 10/2012 | Loeker et al. | |
| 8,309,682 B2 | 11/2012 | Tian et al. | |
| 8,318,306 B2 | 11/2012 | Tian et al. | |
| 8,318,895 B1 | 11/2012 | Tian et al. | |
| 8,361,926 B2 | 1/2013 | Tian et al. | |
| 8,367,774 B2 | 2/2013 | Frank | |
| 8,420,567 B1 | 4/2013 | Naumann et al. | |
| 8,445,596 B2 | 5/2013 | Mertens et al. | |
| 8,466,228 B2 | 6/2013 | Smith et al. | |
| 8,476,189 B1 | 7/2013 | Naumann et al. | |
| 8,486,855 B2 | 7/2013 | Tian et al. | |
| 8,487,049 B2 | 7/2013 | Tian et al. | |
| 8,518,541 B2 | 8/2013 | Loeker et al. | |
| 8,519,041 B2 | 8/2013 | Smith et al. | |
| 8,580,953 B2 | 11/2013 | Frank et al. | |
| 8,653,320 B2 | 2/2014 | Furno et al. | |
| 8,703,645 B2 | 4/2014 | Tian et al. | |
| 8,734,948 B2 | 5/2014 | Tian et al. | |
| 8,802,786 B2 | 8/2014 | Shi et al. | |
| 8,822,582 B2 | 9/2014 | Smith et al. | |
| 8,859,701 B2 * | 10/2014 | Loick | A61L 15/22 264/140 |
| 8,859,758 B2 | 10/2014 | Frank et al. | |
| 8,883,881 B2 | 11/2014 | Smith et al. | |
| 8,906,824 B2 | 12/2014 | Loeker et al. | |
| 8,962,910 B2 | 2/2015 | Azad et al. | |
| 9,737,874 B2 * | 8/2017 | Wattebled | B01J 20/3028 |
| 10,287,379 B2 * | 5/2019 | Loick | A61L 15/225 |
| 2003/0157318 A1 | 8/2003 | Brehm et al. | |
| 2003/0207997 A1 | 11/2003 | Mertens et al. | |
| 2004/0157989 A1 | 8/2004 | Bruhn et al. | |
| 2007/0015860 A1 | 1/2007 | Frank | |
| 2010/0035757 A1 | 2/2010 | Furno et al. | |
| 2010/0247615 A1 * | 9/2010 | Toreki | A61L 15/60 424/447 |
| 2011/0118419 A1 | 5/2011 | Funk et al. | |
| 2012/0145956 A1 | 6/2012 | Walden et al. | |
| 2014/0045683 A1 * | 2/2014 | Loick | A61L 15/22 502/402 |
| 2014/0054497 A1 | 2/2014 | Wattebled et al. | |
| 2014/0257223 A1 | 9/2014 | Henn et al. | |
| 2014/0306155 A1 | 10/2014 | Tian et al. | |
| 2014/0306156 A1 | 10/2014 | Tian et al. | |
| 2014/0309607 A1 | 10/2014 | Richlen et al. | |
| 2014/0316040 A1 | 10/2014 | Shi et al. | |
| 2015/0071870 A1 | 3/2015 | Toreki et al. | |

FOREIGN PATENT DOCUMENTS

| | | |
|---|---|---|
| CN | 102089013 A | 6/2011 |
| CN | 102405063 A | 4/2012 |
| CN | 104039847 A | 9/2014 |
| DE | 2706135 A1 | 8/1978 |
| DE | 3503458 A1 | 8/1985 |
| DE | 4020780 C1 | 8/1991 |
| DE | 4244548 A1 | 7/1994 |
| DE | 4418818 A1 | 1/1995 |
| DE | 4333056 A1 | 3/1995 |
| DE | 19543366 A1 | 5/1997 |
| DE | 19543368 A1 | 5/1997 |
| DE | 19825486 A1 | 2/2000 |
| DE | 19909653 A1 | 9/2000 |
| DE | 19909838 A1 | 9/2000 |
| DE | 19939662 A1 | 2/2001 |
| DE | 10218147 A1 | 11/2003 |
| DE | 10334271 A1 | 2/2005 |
| DE | 102005055497 A1 | 5/2007 |
| EP | 1438354 A1 | 7/2004 |
| EP | 1770113 A1 | 4/2007 |
| WO | 9934843 A1 | 7/1999 |
| WO | 03025054 A1 | 3/2003 |
| WO | 2006062258 A2 | 6/2006 |
| WO | 2010096595 A2 | 8/2010 |
| WO | 2011023560 A2 | 3/2011 |
| WO | WO-2012055681 A1 * | 5/2012 |
| WO | 2013101197 A1 | 7/2013 |
| WO | 2014168858 A1 | 10/2014 |

* cited by examiner

SUPERABSORBENT POLYMERS WITH IMPROVED ODOR CONTROL CAPACITY AND PROCESS FOR THE PRODUCTION THEREOF

This application is a division of and claims priority to U.S. application Ser. No. 14/639,177, filed on Mar. 5, 2015, which claims the benefit of U.S. Provisional Application Ser. No. 61/948,114, filed on Mar. 5, 2014, applications which are incorporated by reference herein in their entirety.

FIELD

The present invention relates to superabsorbent polymers with improved odor control capacity, and to processes for the production thereof.

BACKGROUND

DE 40 20 780 C1 (U.S. Pat. No. 5,409,771 A) discloses the post-treatment of superabsorbent polymers by post-crosslinking the surfaces of the polymer particles. The post-crosslinking of the surface of the water-absorbing polymer particles particularly increases the absorption capacity of the polymer particles under pressure.

DE 199 09 653 A1 (US 2003/207997 A1) and DE 199 09 838 A1 (U.S. Pat. No. 6,605,673 B1) describe pulverulent, surface post-cross-linked polymers which absorb water, aqueous or serous fluids or blood, which are based on monomers bearing acid groups and which have been coated and post-cross-linked with a surface post-crosslinker and a cation in aqueous solution. The polymers disclosed in this prior art have advantageous absorption properties compared to conventional polymers, especially a high permeability.

Hygiene articles such as diapers and incontinent pads, liners and articles containing superabsorbent polymers are designed to absorb bodily fluids such as urine. Urine can generally be a source of two major types of nuisance malodors; one from the bacterial or enzymatic decomposition of urea to form ammonia; the second from organic molecules found in the urine itself. The first odor requires time to develop, i.e. time for the urea to decompose to ammonia, depending on many factors such as the bacteria present on the skin, the pH, the temperature, among others. Odor from organic molecules, usually the byproducts of digestion or other metabolic processes, on the other hand, is present immediately when the urine is excreted from the body. There is a need for a means of controlling, reducing or even eliminating both types of odor.

In the case of prolonged wearing of hygiene articles including absorbent polymers, especially when some of these have already absorbed body fluids such as urine, the organic constituents of the urine and the body heat of the wearer can soon cause an unpleasant odor nuisance. In order to counter this, numerous attempts have been made through appropriate additions in the non-superabsorbent constituents of the hygiene article to achieve binding of the odor-forming substances or to mask the odor by means of perfume or the like. The introduction of such substances in the form of non-superabsorbent constituents often has an adverse effect on the performance of these hygiene articles during wear. For instance, the odor-inhibiting or odor-reducing substances, which are at first spatially separate from the superabsorbent region, may be brought into the region which contains superabsorbent by the introduction of bodily fluids, for example by a washing action, odor where they then exhibit an adverse effect overall on the performance of the superabsorbent and hence of the hygiene article. A further disadvantage of this concept is that the majority of the body fluid released into the hygiene article is in any case present within the superabsorbent, and the odor-inhibiting or odor-reducing substances present outside the superabsorbent are therefore less able to display their effect.

DE 198 25 486 (US 2004/157989 A1) and DE 199 39 662 A1 (US 2003/157318 A1) disclose the combination of superabsorbents with cyclodextrin for odor reduction. However, it can be inferred from this approach, which is indeed promising, that the cyclodextrin exhibits its odor-inhibiting action in the superabsorbent only under particular conditions, namely when it is ensured that the cyclodextrin does not separate again from the superabsorbent. It is preferable in this context that the cyclodextrin is incorporated at least into the surface of the superabsorbent article, by virtue of cyclodextrin and/or cyclodextrin derivatives being covalently and/or ionically bonded and/or incorporated therein.

DE 103 34 271 (US 2007/015860 A1) further discloses superabsorbent agglomerates which may have a multitude of odor binders in homogeneous form in the agglomerate. However, this document, which discloses an excellent solution for the use of fine superabsorbent particles, does not provide superabsorbents having odor-binding properties which are of particularly good suitability for use in hygiene articles. Thus, as well as an efficient and effective use of the odor binders, the superabsorbent properties influenced by this odor binders are also still in need of improvement.

DE-A-10 2005 055 497 (US 2010/035757 A1) teaches imparting improved odor-binding properties to superabsorbent polymers by contacting with metal salts of ricinoleic acid and/or with amino acids.

Other approaches such as the use of lower pH additives, enzyme inhibitors, chelants and the like, are only effective in delaying the formation of ammonia from urea and have little effect on organic molecule odor, or only address a small fraction of the types of organic odor. One of the difficulties with controlling, reducing or eliminating organic odor is the large variety of chemistries of the organic malodor molecules, including ketones and aldehydes, amines, mercaptans, sulfides, cyclic compounds, unsaturated compounds and aromatics and the like. Only addressing one or two classes of organic odor does little to reduce the overall nuisance created by urine malodors.

SUMMARY

In general terms, the problem addressed by the present invention was that of alleviating or even overcoming the disadvantages arising from the prior art.

One problem addressed by the invention was that of providing a water-absorbing polymer which firstly possesses good odor-binding and/or -reducing properties. Secondly, there is a need for a water-absorbing polymer with multiple odor control, that is to say, the ability to reduce or eliminate odors from ammonia and organic molecules. Third, the organic odor control must be effective on a wide range of organic molecule odors, not just one or two chemical classes. At the same time, it is to be ensured that the performance of the hygiene article including this odor-binding and -reducing water-absorbing polymer is essentially just as good as or even better than the performance of the hygiene article comprising a superabsorbent which odor does not include the odor binder. More particularly, the performance properties of the water-absorbing polymer were to be influenced to a minimum degree or at most slightly by the use of odor-binding additives, which are to be used in minimum amounts. Advantageously, the performance properties of the water-absorbing polymer are in some cases actually to be improved by the addition of the odor-binding or -reducing additive.

In addition, the water-absorbing polymer, on contact with aqueous body fluids, more particularly with urine or iron-containing fluids, for example blood or menstrual fluids, was to have a minimum tendency to severe discoloration.

Furthermore, a problem addressed by the invention was that of providing a process by which such a water-absorbing polymer can be obtained. Moreover, a problem addressed by the invention was that of providing a hygiene article which, as well as good odor-binding and odor-reducing properties for the multiple sources of urine malodors, also exhibits good absorption performance. Another problem addressed by the present invention was that of providing water-absorbing polymers which can generally be incorporated into composites or else can be used as a composite or as such in chemical products or constituents thereof.

These objects are achieved by the subject-matter of the independent claims. Advantageous configurations and developments which can occur individually or in combination form the subject-matter of the dependent claims in each case.

DETAILED DESCRIPTION

A contribution to the solution of the problem stated at the outset is made by an inventive water-absorbing polymer comprising:

($\alpha$1) 20-99.999% by weight, preferably 55-98.99% by weight and more preferably 70-98.79% by weight of polymerized, ethylenically unsaturated monomers bearing acid groups, or salts thereof, or polymerized, ethylenically unsaturated monomers including a protonated or quaternized nitrogen, or mixtures thereof, particular preference being given to mixtures including at least ethylenically unsaturated monomers containing acid groups, preferably acrylic acid, ($\alpha$2) 0-80% by weight, preferably 0-44.99% by weight and more preferably 0.1-44.89% by weight of polymerized, monoethylenically unsaturated monomers copolymerizable with ($\alpha$1), ($\alpha$3) 0.001-5% by weight, preferably 0.01-3% by weight and more preferably 0.01-2.5% by weight of one or more crosslinkers, ($\alpha$4) 0-30% by weight, preferably 0-5% by weight and more preferably 0.1-5% by weight of a water-soluble polymer, ($\alpha$5) 0-20% by weight, preferably 2.5-15% by weight and more preferably 5-10% by weight of water, and ($\alpha$6) 0-20% by weight, preferably 0-10% by weight and more preferably 0.1-8% by weight of one or more additives, where the sum of the weights of ($\alpha$1) to ($\alpha$6) is 100% by weight, wherein the water-absorbing polymer has been treated with 0.0001 to 3% by weight, preferably 0.0002 to 2% by weight and more preferably 0.0007 to 1.8% by weight of a peroxo compound, based on the acrylic acid, after the polymerization. Preferred are water-absorbing polymers with 0.0001 to 1.5% by weight of a peroxo compound, based on the acrylic acid, added after the polymerization.

Peroxo compounds in the context of the present inventions are understood to mean those from the group of organic and inorganic peroxo compounds.

In the context of the present invention, the term "inorganic peroxo compounds" is preferably understood to mean those from the group of alkali metal or alkaline earth metal peroxomonosulphate, or peroxodisulphate. The inorganic peroxo compounds selected are preferably those from the group of alkali metal or alkaline earth metal peroxomonosulphate, or peroxodisulphate, sulpho monoperacid, peroxomonosulphate triple salt (Caro's acid), most preferably peroxomonosulphate triple salt.

In the context of the present invention, the term "organic peroxo compounds" is preferably understood to mean those from the group of carbamide peroxo, peroxocarboxylic acids, more preferably peroxocarboxylic acids.

Water-absorbing polymers which have been treated with the above listed peroxo compounds possess excellent odor-binding and -reducing properties for both ammonia-type and organic-type odors. The performance of the hygiene article including the "peroxo compound treated" water-absorbing polymer is in many cases as good as or even better than the performance of the hygiene article comprising a superabsorbent without the peroxo compounds. Surprisingly, even discoloration is not severe in the "peroxo compound treated" water-absorbing polymers. Best results are achieved with the inorganic peroxo compounds which are therefore preferred according to the invention. Especially inorganic peroxo compounds from the group of alkali metal or alkaline earth metal peroxomonosulphate, or peroxodisulphate, sulpho monoperacid and most of all peroxomonosulphate triple salt (Caro's acid), added in the before described and preferred weight % ranges, resulted in water-absorbing polymers with excellent odor-binding properties.

Inorganic peroxo Salts involve metals from the group of the alkali metals, alkaline earth metals and the boron group. Preference is given here to the metals from the group of sodium, potassium, caesium, rubidium, magnesium, calcium, strontium, barium, aluminum, gallium, indium. Particular preference is given to those from the group of sodium, potassium, calcium, magnesium, and optionally mixtures of these. Particular preference is given to metals from the group of sodium, potassium, calcium and magnesium.

In this context, water-absorbing polymer structures preferred in accordance with the invention are especially fibers, foams or particles, fibers and particles being particularly preferred and particles most preferred.

The dimensions of polymer fibers preferred in accordance with the invention are such that they can be incorporated into or as yarns for textiles, and also directly into textiles. It is preferable in accordance with the invention that the polymer fibers have a length in the range from 1 to 500 mm, preferably 2 to 500 mm and more preferably 5 to 100 mm, and a diameter in the range from 1 to 200 denier, preferably from 3 to 100 denier, and more preferably from 5 to 60 denier.

The dimensions of polymer particles preferred in accordance with the invention are such that they have a mean particle size to ERT 420.2-02 in the range from 10 to 3000 µm, preferably from 20 to 2000 µm and more preferably from 150 to 850 µm or from 150 to 600 µm. In this context, it is especially preferable that the proportion of the polymer particles having a particle size within a range from 300 to 600 µm is at least 30% by weight, more preferably at least 40% by weight, further preferably at least 50% by weight and most preferably at least 75% by weight, based on the total weight of the water-absorbing polymer particles. In another embodiment of the inventive water-absorbing polymer structure, the proportion of the polymer particles having a particle size within a range from 150 to 850 µm is at least 50% by weight, more preferably at least 75% by weight, further preferably at least 90% by weight and most preferably at least 95% by weight, based on the total weight of the water-absorbing polymer particles.

The monoethylenically unsaturated monomers ($\alpha 1$) containing acid groups may be partly or fully neutralized, preferably partly. The monoethylenically unsaturated monomers containing acid groups have preferably been neutralized to an extent of at least 10 mol %, more preferably to an extent of at least from 25 to 50 mol % and further preferably to an extent of from 50 to 90 mol %. The neutralization of the monomers ($\alpha 1$) may precede or else follow the polymerization. In this case, the partial neutralization is effected to an extent of at least 10 mol %, more preferably to an extent of at least from 25 to 50 mol % and further preferably to an extent of 50 to 90 mol %. Moreover, neutralization can be effected with alkali metal hydroxides, alkaline earth metal hydroxides, ammonia, and carbonates and bicarbonates. In addition, any further base which forms a water-soluble salt with the acid is conceivable. Mixed neutralization with different bases is also conceivable. Preference is given to neutralization with ammonia or with alkali metal hydroxides, more preferably with sodium hydroxide or with ammonia.

In addition, the free acid groups in a polymer may predominate, such that this polymer has a pH within the acidic range. This acidic water-absorbing polymer may be at least partly neutralized by a polymer with free basic groups, preferably amine groups, which is basic compared to the acid polymer. These polymers are referred to in the literature as "Mixed-Bed Ion-Exchange Absorbent Polymers" (MBIEA polymers) and are disclosed in WO 99/34843 inter alia. The disclosure of WO 99/34843 is hereby incorporated by reference and is thus considered to form part of the disclosure. In general, MBIEA polymers constitute a composition which includes firstly basic polymers capable of exchanging anions, and secondly a polymer which is acidic compared to the basic polymer and is capable of exchanging cations. The basic polymer has basic groups and is typically obtained by the polymerization of monomers which bear basic groups or groups which can be converted to basic groups. These monomers are in particular those which have primary, secondary or tertiary amines or the corresponding phosphines, or at least two functional groups. This group of monomers includes especially ethyleneamine, allylamine, diallylamine, 4-aminobutene, alkyloxycyclines, vinylformamide, 5-aminopentene, carbodiimide, formaldacine, melamine and the like, and the secondary or tertiary amine derivatives thereof.

Preferred monoethylenically unsaturated monomers ($\alpha 1$) containing acid groups are acrylic acid, methacrylic acid, ethacrylic acid, $\alpha$-chloroacrylic acid, $\alpha$-cyanoacrylic acid, $\beta$-methylacrylic acid (crotonic acid), $\alpha$-phenylacrylic acid, $\beta$-acryloyloxypropionic acid, sorbic acid, $\alpha$-chlorosorbic acid, 2'-methylisocrotonic acid, cinnamic acid, p-chlorocinnamic acid, $\beta$-stearyl acid, itaconic acid, citraconic acid, mesaconic acid, glutaconic acid, aconitic acid, maleic acid, fumaric acid, tricarboxyethylene and maleic anhydride, preference being given particularly to acrylic acid and methacrylic acid with acrylic acid being especially preferred.

In addition to these monomers containing carboxylate groups, preferred monoethylenically unsaturated monomers ($\alpha 1$) containing acid groups additionally include ethylenically unsaturated sulphonic acid monomers or ethylenically unsaturated phosphonic acid monomers.

Preferred ethylenically unsaturated sulphonic acid monomers are allylsulphonic acid or aliphatic or aromatic vinylsulphonic acids or acrylic or methacrylic sulphonic acids. Preferred aliphatic or aromatic vinylsulphonic acids are vinylsulphonic acid, 4-vinylbenzylsulphonic acid, vinyltoluenesulphonic acid and styrenesulphonic acid. Preferred acryloyl- or methacryloylsulphonic acids are sulphoethyl (meth)acrylate, sulphopropyl (meth)acrylate, 2-hydroxy-3-methacryloyloxypropylsulphonic acid, and (meth)acrylamidoalkylsulphonic acids such as 2-acrylamido-2-methylpropanesulphonic acid.

Preferred ethylenically unsaturated phosphonic acid monomers are vinylphosphonic acid, allylphosphonic acid, vinylbenzylphosphonic acid, (meth)acrylamidoalkylphosphonic acids, acrylamidoalkyldiphosphonic acids, phosphonomethylated vinylamines and (meth)acryloylphosphonic acid derivatives.

Preferred ethylenically unsaturated monomers ($\alpha 1$) containing a protonated nitrogen are preferably dialkylaminoalkyl (meth)acrylates in protonated form, for example dimethylaminoethyl (meth)acrylate hydrochloride or dimethylaminoethyl (meth)acrylate hydrosulphate, and dialkylaminoalkyl(meth)acrylamides in protonated form, for example dimethylaminoethyl(meth)acrylamide hydrochloride, dimethylaminopropyl(meth)acrylamide hydrochloride, dimethylaminopropyl(meth)acrylamide hydrosulphate or dimethylaminoethyl(meth)acrylamide hydrosulphate.

Preferred ethylenically unsaturated monomers ($\alpha 1$) containing a quaternized nitrogen are dialkylammonioalkyl (meth)acrylates in quaternized form, for example trimethylammonioethyl (meth)acrylate methosulphate or dimethylethylammonioethyl (meth)acrylate ethosulphate, and (meth)acrylamidoalkyldialkylamines in quaternized form, for example (meth)acrylamidopropyltrimethylammonium chloride, trimethylammonioethyl (meth)acrylate chloride or (meth)acrylamidopropyltrimethylammonium sulphate.

Preferred monoethylenically unsaturated monomers ($\alpha 2$) copolymerizable with ($\alpha 1$) are acrylamides and methacrylamides.

Preferred (meth)acrylamides are, in addition to acrylamide and methacrylamide, alkyl-substituted (meth)acrylamides or aminoalkyl-substituted derivatives of (meth)acrylamide, such as N-methylol(meth)acrylamide, N,N-dimethylamino(meth)acrylamide, dimethyl(meth)acrylamide or diethyl(meth)acrylamide. Possible vinylamides are, for example, N-vinylamides, N-vinylformamides, N-vinylacetamides, N-vinyl-N-methylacetamides, N-vinyl-N-methylformamides, vinylpyrrolidone. Among these monomers, particular preference is given to acrylamide.

Additionally preferred as monoethylenically unsaturated monomers ($\alpha 2$) copolymerizable with ($\alpha 1$) are water-dispersible monomers. Preferred water-dispersible monomers are acrylic esters and methacrylic esters, such as methyl (meth)acrylate, ethyl (meth)acrylate, propyl (meth)acrylate or butyl (meth)acrylate, and also vinyl acetate, styrene and isobutylene.

Crosslinkers ($\alpha 3$) preferred in accordance with the invention are compounds having at least two ethylenically unsaturated groups within one molecule (crosslinker class I), compounds having at least two functional groups which can react with functional groups of monomers ($\alpha 1$) or ($\alpha 2$) in a condensation reaction (=condensation crosslinkers), in an addition reaction or in a ring-opening reaction (crosslinker class II), compounds which have at least one ethylenically unsaturated group and at least one functional group which can react with functional groups of monomers ($\alpha 1$) or ($\alpha 2$) in a condensation reaction, in an addition reaction or in a ring-opening reaction (crosslinker class III), or polyvalent metal cations (crosslinker class IV). The compounds of crosslinker class I achieve crosslinking of the polymers through the free-radical polymerization of the ethylenically unsaturated groups of the crosslinker molecule with the monoethylenically unsaturated monomers ($\alpha$1) or ($\alpha$2), while the compounds of the crosslinker class II and the polyvalent metal cations of crosslinker class IV achieve crosslinking of the polymers by a condensation reaction of the functional groups (crosslinker class II) or by electrostatic interaction of the polyvalent metal cation (crosslinker class IV) with the functional groups of monomers ($\alpha$1) or ($\alpha$2). In the case of the compounds of crosslinker class III, there is correspondingly crosslinking of the polymer both by free-radical polymerization of the ethylenically unsaturated group and by a condensation reaction between the functional group of the crosslinker and the functional groups of monomers ($\alpha$1) or ($\alpha$2).

Preferred compounds of crosslinker class I are poly(meth)acrylic esters which are obtained, for example, by the reaction of a polyol, for example ethylene glycol, propylene glycol, trimethylolpropane, 1,6-hexanediol, glycerol, pentaerythritol, polyethylene glycol or polypropylene glycol, of an amino alcohol, of a polyalkylenepolyamine, for example diethylenetriamine or triethylenetetramine, or of an alkoxylated polyol with acrylic acid or methacrylic acid. Preferred compounds of crosslinker class I are additionally polyvinyl compounds, poly(meth)allyl compounds, (meth)acrylic esters of a monovinyl compound or (meth)acrylic esters of a mono(meth)allyl compound, preferably of the mono(meth)allyl compounds of a polyol or of an amino alcohol. In this context, reference is made to DE 195 43 366 (U.S. Pat. No. 6,087,450 A) and DE 195 43 368 (U.S. Pat. No. 6,143,821 A). The disclosures are hereby incorporated by reference and are thus considered to form part of the disclosure.

Examples of compounds of crosslinker class I include alkenyl di(meth)acrylates, for example ethylene glycol di(meth)acrylate, 1,3-propylene glycol di(meth)acrylate, 1,4-butylene glycol di(meth)acrylate, 1,3-butylene glycol di(meth)acrylate, 1,6-hexanediol di(meth)acrylate, 1,10-decanediol di(meth)acrylate, 1,12-dodecanediol di(meth)acrylate, 1,18-octadecanediol di(meth)acrylate, cyclopentanediol di(meth)acrylate, neopentyl glycol di(meth)acrylate, methylene di(meth)acrylate or pentaerythritol di(meth)acrylate, alkenyldi(meth)acrylamides, for example N-methyldi(meth)acrylamide, N,N'-3-methylbutylidenebis(meth)acrylamide, N,N'-(1,2-dihydroxyethylene)bis(meth)acrylamide, N,N'-hexamethylenebis(meth)acrylacrylamide or N,N'-methylenebis(meth)acrylamide, polyalkoxy di(meth)acrylates, for example diethylene glycol di(meth)acrylate, triethylene glycol di(meth)acrylate, tetraethylene glycol di(meth)acrylate, dipropylene glycol di(meth)acrylate, tripropylene glycol di(meth)acrylate or tetrapropylene glycol di(meth)acrylate, bisphenol A di(meth)acrylate, ethoxylated bisphenol A di(meth)acrylate, benzylidene di(meth)acrylate, 1,3-di(meth)acryloyloxy-2-propanol, hydroquinone di(meth)acrylate, di(meth)acrylate esters of trimethylolpropane which has preferably been alkoxylated, preferably ethoxylated, with 1 to 30 mol of alkylene oxide per hydroxyl group, thioethylene glycol di(meth)acrylate, thiopropylene glycol di(meth)acrylate, thiopolyethylene glycol di(meth)acrylate, thiopolypropylene glycol di(meth)acrylate, divinyl ethers, for example 1,4-butanediol divinyl ether, divinyl esters, for example divinyl adipate, alkanedienes, for example butadiene or 1,6-hexadiene, divinylbenzene, di(meth)allyl compounds, for example di(meth)allyl phthalate or di(meth)allyl succinate, homo- and copolymers of di(meth)allyldimethylammonium chloride and homo- and copolymers of diethyl(meth)allylaminomethyl (meth)acrylate ammonium chloride, vinyl (meth)acryloyl compounds, for example vinyl (meth)acrylate, (meth)allyl (meth)acryloyl compounds, for example (meth)allyl (meth)acrylate, (meth)allyl (meth)acrylate ethoxylated with 1 to 30 mol of ethylene oxide per hydroxyl group, di(meth)allyl esters of polycarboxylic acids, for example di(meth)allyl maleate, di(meth)allyl fumarate, di(meth)allyl succinate or di(meth)allyl terephthalate, compounds having 3 or more ethylenically unsaturated, free-radically polymerizable groups, for example glyceryl tri(meth)acrylate, (meth)acrylate esters of glycerol which has been ethoxylated with preferably 1 to 30 mol of ethylene oxide per hydroxyl group, trimethylolpropane tri(meth)acrylate, tri(meth)acrylate esters of trimethylolpropane which has preferably been alkoxylated, preferably ethoxylated, with 1 to 30 mol of alkylene oxide per hydroxyl group, trimethacrylamide, (meth)allylidene di(meth)acrylate, 3-allyloxy-1,2-propanediol di(meth)acrylate, tri(meth)allyl cyanurate, tri(meth)allyl isocyanurate, pentaerythritol tetra(meth)acrylate, pentaerythritol tri(meth)acrylate, (meth)acrylic esters of pentaerythritol ethoxylated with preferably 1 to 30 mol of ethylene oxide per hydroxyl group, tris(2-hydroxyethyl) isocyanurate tri(meth)acrylate, trivinyl trimellitate, tri(meth)allylamine, di(meth)allylalkylamines, for example di(meth)allylmethylamine, tri(meth)allyl phosphate, tetra(meth)allylethylenediamine, poly(meth)allyl esters, tetra(meth)allyloxyethane or tetra(meth)allylammonium halides.

Preferred compounds of crosslinker class II are compounds which have at least two functional groups which can react in a condensation reaction (=condensation crosslinkers), in an addition reaction or in a ring-opening reaction with the functional groups of monomers ($\alpha$1) or ($\alpha$2), preferably with acid groups of monomers ($\alpha$1). These functional groups of the compounds of crosslinker class II are preferably alcohol, amine, aldehyde, glycidyl, isocyanate, carbonate, or epichloro functions.

Examples of compounds of crosslinker class II include polyols, for example ethylene glycol, polyethylene glycols such as diethylene glycol, triethylene glycol and tetraethylene glycol, propylene glycol, polypropylene glycols such as dipropylene glycol, tripropylene glycol or tetrapropylene glycol, 1,3-butanediol, 1,4-butanediol, 1,5-pentanediol, 2,4-pentanediol, 1,6-hexanediol, 2,5-hexanediol, glycerol, polyglycerol, trimethylolpropane, polyoxypropylene, oxyethylene-oxypropylene block copolymers, sorbitan fatty acid esters, polyoxyethylene sorbitan fatty acid esters, pentaerythritol, polyvinyl alcohol and sorbitol, amino alcohols, for example ethanolamine, diethanolamine, triethanolamine or propanolamine, polyamine compounds, for example ethylenediamine, diethylenetriamine, triethylenetetramine, tetraethylenepentamine or pentaethylenehexamine, polyglycidyl ether compounds such as ethylene glycol diglycidyl ether, polyethylene glycol diglycidyl ether, glyceryl diglycidyl ether, glyceryl polyglycidyl ether, pentaerythrityl polyglycidyl ether, propylene glycol diglycidyl ether, polypropylene glycol diglycidyl ether, neopentyl glycol diglycidyl ether, hexanediol glycidyl ether, trimethylolpropane polyglycidyl ether, sorbitol polyglycidyl ether, diglycidyl phthalate, adipic acid diglycidyl ether, 1,4-phenylenebis(2-oxazoline), glycidol, polyisocyanates, preferably diisocyanates such as toluene 2,4-diisocyanate and hexamethylene diisocyanate, polyaziridine compounds such as 2,2-bishydroxymethylbutanol tris[3-(1-aziridinyl)propionate], 1,6-hexamethylenediethyleneurea and diphenylmethanebis-4,4'-N,N'-diethyleneurea, halogen peroxides, for example epichloro- and epibromohydrin and $\alpha$-methylepichlorohydrin, alkylene carbonates such as 1,3-dioxolan-2-one (ethylene carbonate), 4-methyl-1,3-dioxolan-2-one (propylene carbonate), 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one, 1,3-dioxolan-2-one, poly-1,3-dioxolan-2-one, polyquaternary amines such as condensation products of dimethylamines and epichlorohydrin. Preferred compounds of crosslinker class II are additionally polyoxazolines such as 1,2-ethylenebisoxazoline, crosslinkers with silane groups, such as α-glycidoxypropyltrimethoxysilane and α-aminopropyltrimethoxysilane, oxazolidinones such as 2-oxazolidinone, bis- and poly-2-oxazolidinones and diglycol silicates.

Preferred compounds of class III include hydroxyl- or amino-containing esters of (meth)acrylic acid, for example 2-hydroxyethyl (meth)acrylate and 2-hydroxypropyl (meth)acrylate, and also hydroxyl- or amino-containing (meth)acrylamides or mono(meth)allyl compounds of diols.

The polyvalent metal cations of crosslinker class IV derive preferably from mono- or polyvalent cations, the monovalent especially from alkali metals such as potassium, sodium, lithium, preference being given to lithium. Preferred divalent cations derive from zinc, beryllium, alkaline earth metals such as magnesium, calcium, strontium, preference being given to magnesium. Further higher-valency cations usable in accordance with the invention are cations of aluminum, iron, chromium, manganese, titanium, zirconium and other transition metals, and also double salts of such cations or mixtures of the salts mentioned. Preference is given to using aluminum salts and alums and the different hydrates thereof, for example $AlCl_3 \times 6H_2O$, $NaAl(SO_4)_2 \times 12 H_2O$, $KAl(SO_4)_2 \times 12 H_2O$ or $Al_2(SO_4)_3 \times 14\text{-}18 H_2O$. Particular preference is given to using $Al_2(SO_4)_3$ and hydrates thereof as crosslinkers of crosslinking class IV.

The superabsorbent particles used in the process according to the invention are preferably crosslinked by crosslinkers of the following crosslinker classes, or by crosslinkers of the following combinations of crosslinker classes: I, II, III, IV, III, I III, I IV, I II III, I II IV, I III IV, II III IV, II IV or III IV. The above combinations of crosslinker classes are each a preferred embodiment of crosslinkers of a superabsorbent particle used in the process according to the invention.

Further preferred embodiments of the superabsorbent particles used in the process according to the invention are polymers which are crosslinked by any of the aforementioned crosslinkers of crosslinker class I. Among these, preference is given to water-soluble crosslinkers. In this context, particular preference is given to N,N'-methylenebisacrylamide, polyethylene glycol di(meth)acrylates, triallylmethylammonium chloride, tetraallylammonium chloride, and allyl nonaethylene glycol acrylate prepared with 9 mol of ethylene oxide per mole of acrylic acid.

As water-soluble polymers (α4), the superabsorbent particles may comprise water-soluble polymers, such as partly or fully hydrolyzed polyvinyl alcohol, polyvinylpyrrolidone, starch or starch derivatives, polyglycols or polyacrylic acid, preferably incorporated in polymerized form. The molecular weight of these polymers is uncritical provided that they are water-soluble. Preferred water-soluble polymers are starch or starch derivatives or polyvinyl alcohol. The water-soluble polymers, preferably synthetic water-soluble polymers such as polyvinyl alcohol, can also serve as a graft base for the monomers to be polymerized.

The additives (α5) present in the polymers are organic or inorganic substances, for example odor binders, especially zeolites or cyclodextrins, skincare substances, surfactants or antioxidants.

The preferred organic additives include cyclodextrins or derivatives thereof, and polysaccharides. Also preferred are cellulose and cellulose derivatives such as CMC, cellulose ethers. Preferred cyclodextrins or cyclodextrin derivatives are those compounds disclosed in DE-A-198 25 486 at page 3 line 51 to page 4 line 61 (corresponds to US 2004/157989 A1). The aforementioned section of this published patent application is hereby incorporated by reference and is considered to form part of the disclosure of the present invention. Particularly preferred cyclodextrins are underivatized α-, β-, γ- or δ-cyclodextrins.

The inorganic particulate additives used may be any materials which are typically used to modify the properties of water-absorbing polymers. The preferred inorganic additives include sulphates such as $Na_2SO_4$, lactates, for instance sodium lactate, silicates, especially framework silicates such as zeolites, or silicates which have been obtained by drying aqueous silica solutions or silica sols, for example the commercially available products such as precipitated silicas and fumed silicas, for example Aerosils having a particle size in the range from 5 to 50 nm, preferably in the range from 8 to 20 nm, such as "Aerosil 200" from Evonik Industries AG, aluminates, titanium dioxides, zinc oxides, clay materials, and further minerals familiar to those skilled in the art, and also carbonaceous inorganic materials.

Preferred silicates are all natural or synthetic silicates which are disclosed as silicates in Hollemann and Wiberg, Lehrbuch der Anorganischen Chemie [Inorganic Chemistry], Walter de Gruyter-Verlag, 91st-100th edition, 1985, on pages 750 to 783. The aforementioned section of this textbook is hereby incorporated by reference and is considered to form part of the disclosure of the present invention.

Particularly preferred silicates are the zeolites. The zeolites used may be all synthetic or natural zeolites known to those skilled in the art. Preferred natural zeolites are zeolites from the natrolite group, the harmotone group, the mordenite group, the chabasite group, the faujasite group (sodalite group) or the analcite group. Examples of natural zeolites are analcime, leucite, pollucite, wairakite, bellbergite, bikitaite, boggsite, brewsterite, chabasite, willhendersonite, cowlesite, dachiardite, edingtonite, epistilbite, erionite, faujasite, ferrierite, amicite, garronite, gismondine, gobbinsite, gmelinite, gonnardite, goosecreekite, harmotone, phillipsite, wellsite, clinoptilolite, heulandite, laumontite, levyne, mazzite, merlinoite, montesommaite, mordenite, mesolite, natrolite, scolecite, offretite, paranatrolite, paulingite, perlialite, barrerite, stilbite, stellerite, thomsonite, tschernichite or yugawaralite. Preferred synthetic zeolites are zeolite A, zeolite X, zeolite Y, zeolite P, or the product ABSCENTS®.

The zeolites used may be zeolites of what is called the "intermediate" type, in which the $SiO_2/AlO_2$ ratio is less than 10; the $SiO_2/AlO_2$ ratio of these zeolites is more preferably within a range from 2 to 10. In addition to these "intermediate" zeolites, it is also possible to use zeolites of the "high" type, which include, for example, the known "molecular sieve" zeolites of the ZSM type, and β-zeolite. These "high" zeolites are preferably characterized by an $SiO_2/AlO_2$ ratio of at least 35, more preferably by an $SiO_2/AlO_2$ ratio within a range from 200 to 500.

The aluminates used are preferably the naturally occurring spinels, especially common spinel, zinc spinel, iron spinel or chromium spinel.

Preferred titanium dioxide is pure titanium dioxide in the rutile, anatase and brookite crystal forms, and also iron-containing titanium dioxides, for example ilmenite, calcium-containing titanium dioxides such as titanite or perovskite.

Preferred clay materials are those disclosed as clay materials in Hollemann and Wiberg, Lehrbuch der Anorganischen Chemie, Walter de Gruyter-Verlag, 91st-100th edition, 1985, on pages 783 to 785. Particularly the aforementioned section of this textbook is hereby incorporated by reference and is considered to form part of the disclosure of the present invention. Particularly preferred clay materials are kaolinite, illite, halloysite, montmorillonite and talc.

Further inorganic fines preferred in accordance with the invention are the metal salts of the mono-, oligo- and polyphosphoric acids. Among these, preference is given especially to the hydrates, particular preference being given to the mono- to decahydrates and trihydrates. Useful metals include especially alkali metals and alkaline earth metals, preference being given to the alkaline earth metals. Among these, Mg and Ca are preferred and Mg is particularly preferred. In the context of phosphates, phosphoric acids and metal compounds thereof, reference is made to Hollemann and Wiberg, Lehrbuch der Anorganischen Chemie, Walter de Gruyter-Verlag, 91st-100th edition, 1985, on pages 651 to 669. The aforementioned section of this textbook is hereby incorporated by reference and is considered to form part of the disclosure of the present invention.

Preferred carbonaceous but nonorganic additives are those pure carbons which are mentioned as graphites in Hollemann and Wiberg, Lehrbuch der Anorganischen Chemie, Walter de Gruyter-Verlag, 91st-100th edition, 1985, on pages 705 to 708. The aforementioned section of this textbook is hereby incorporated by reference and is considered to form part of the disclosure of the present invention. Particularly preferred graphites are synthetic graphites, for example coke, pyrographite, activated carbon or carbon black.

The water-absorbing polymers obtained in the process according to the invention are preferably obtainable by first preparing a hydrogel polymer in particulate form from the aforementioned monomers and crosslinkers. This starting material for the water-absorbing polymers is produced, for example, by bulk polymerization which is preferably effected in kneading reactors such as extruders, solution polymerization, spray polymerization, inverse emulsion polymerization or inverse suspension polymerization. Preference is given to performing the solution polymerization in water as a solvent. The solution polymerization can be effected continuously or batchwise. The prior art discloses a wide spectrum of possible variations with regard to reaction conditions, such as temperatures, type and amount of the initiators, and of the reaction solution. Typical processes are described in the following patents: U.S. Pat. No. 4,286,082, DE 27 06 135, U.S. Pat. No. 4,076,663, DE 35 03 458, DE 40 20 780, DE 42 44 548, DE 43 23 001, DE 43 33 056, DE 44 18 818. The disclosures are hereby incorporated by reference and are thus considered to form part of the disclosure.

The initiators used to initiate the polymerization may be all initiators which form free radicals under the polymerization conditions and are typically used in the production of superabsorbents. These include thermal initiators, redox initiators and photoinitiators, which are activated by means of high-energy radiation. The polymerization initiators may be present dissolved or dispersed in a solution of inventive monomers. Preference is given to the use of water-soluble initiators.

Useful thermal initiators include all compounds which decompose to free radicals when heated and are known to those skilled in the art. Particular preference is given to thermal polymerization initiators having a half-life of less than 10 seconds, further preferably of less than 5 seconds at less than 180° C., further preferably at less than 140° C. Peroxides, hydroperoxides, hydrogen peroxide, persulphates and azo compounds are particularly preferred thermal polymerization initiators. In some cases, it is advantageous to use mixtures of different thermal polymerization initiators. Among these mixtures, preference is given to those of hydrogen peroxide and sodium peroxodisulphate or potassium peroxodisulphate, which can be used in any conceivable ratio. Suitable organic peroxides are preferably acetylacetone peroxide, methyl ethyl ketone peroxide, benzoyl peroxide, lauroyl peroxide, acetyl peroxide, capryl peroxide, isopropyl peroxydicarbonate, 2-ethylhexyl peroxydicarbonate, t-butyl hydroperoxide, cumene hydroperoxide, t-amyl perpivalate, t-butyl perpivalate, t-butyl perneohexanoate, t-butyl isobutyrate, t-butyl per-2-ethylhexenoate, t-butyl perisononanoate, t-butyl permaleate, t-butyl perbenzoate, t-butyl 3,5,5-trimethylhexanoate and amyl perneodecanoate. Further preferred thermal polymerization initiators are: azo compounds such as azobisisobutyronitrile, azobisdimethylvaleronitrile, 2,2'-azobis(2-amidinopropane) dihydrochloride, azobisamidinopropane dihydrochloride, 2,2'-azobis(N,N-dimethylene)isobutyramidine dihydrochloride, 2-(carbamoylazo)isobutyronitrile and 4,4'-azobis(4-cyanovaleric acid). The compounds mentioned are used in customary amounts, preferably within a range from 0.01 to 5 mol %, preferably from 0.1 to 2 mol %, based in each case on the amount of the monomers to be polymerized.

The redox initiators comprise, as the oxidizing component, at least one of the above-specified per compounds, and, as the reducing component, preferably ascorbic acid, glucose, sorbose, mannose, ammonium hydrogensulphite, sulphate, thiosulphate, hyposulphite or sulphide, alkali metal hydrogensulphite, sulphate, thiosulphate, hyposulphite or sulphide, metal salts such as iron(II) ions or silver ions, or sodium hydroxymethylsulphoxylate. The reducing component used in the redox initiator is preferably ascorbic acid or sodium pyrosulphite. Based on the amount of monomers used in the polymerization, $1 \times 10^{-5}$ to 1 mol % of the reducing component of the redox initiator and $1 \times 10^{-5}$ to 5 mol % of the oxidizing component of the redox initiator are used. Instead of the oxidizing component of the redox initiator, or in addition thereto, it is possible to use one or more, preferably water-soluble, azo compounds.

If the polymerization is triggered by the action of high-energy radiation, it is customary to use what are called photoinitiators as the initiator. These may be, for example, what are called α-splitters, H-abstracting systems, or else azides. Examples of such initiators are benzophenone derivatives such as Michler's ketone, phenanthrene derivatives, fluorene derivatives, anthraquinone derivatives, thioxanthone derivatives, coumarin derivatives, benzoin ethers and derivatives thereof, azo compounds such as the above-mentioned free-radical formers, substituted hexaarylbisimidazoles or acylphosphine oxides. Examples of azides are: 2-(N,N-dimethylamino)ethyl 4-azidocinnamate, 2-(N,N-dimethylamino)ethyl 4-azidonaphthyl ketone, 2-(N,N-dimethylamino)ethyl 4-azidobenzoate, 5-azido-1-naphthyl 2'-(N,N-dimethylamino) ethyl sulphone, N-(4-sulphonylazidophenyl)maleimide, N-acetyl-4-sulphonylazidoaniline, 4-sulphonylazidoaniline, 4-azidoaniline, 4-azidophenacyl bromide, p-azidobenzoic acid, 2,6-bis(p-azidobenzylidene)cyclohexanone and 2,6-bis (p-azido-benzylidene)-4-methylcyclohexanone. If they are used, the photoinitiators are employed typically in amounts of 0.01 to 5% by weight, based on the monomers to be polymerized.

Preference is given in accordance with the invention to using an initiator system consisting of hydrogen peroxide, sodium peroxodisulphate and ascorbic acid. In general, the polymerization is initiated with the initiators within a temperature range from 0° C. to 90° C.

The polymerization reaction can be triggered by one initiator or by a plurality of interacting initiators. In addition, the polymerization can be performed in such a way that one or more redox initiators are first added. Later in the polymerization, thermal initiators or photoinitiators are then applied additionally, and the polymerization reaction in the case of photoinitiators is then initiated by the action of high-energy radiation. The reverse sequence, i.e. the initial initiation of the reaction by means of high-energy radiation and photoinitiators or thermal initiators and initiation of the polymerization by means of one or more redox initiators later in the polymerization, is also conceivable.

In order to convert the hydrogel polymers thus obtained to a particulate form, they can first, after they have been comminuted or coarsely divided, be dried at a temperature within a range from 20 to 300° C., preferably within a range from 50 to 250° C. and more preferably within a range from 100 to 200° C., down to a water content of less than 40% by weight, preferably of less than 20% by weight and further preferably of less than 10% by weight, based in each case on the total weight of the hydrogel polymer. The drying is effected preferably in ovens or driers known to those skilled in the art, for example in belt driers, staged driers, rotary tube ovens, fluidized bed driers, pan driers, paddle driers or infrared driers.

According to the present invention, the milling or grinding of the dried polymer is preferably effected by dry grinding, preferably by dry grinding in a hammer mill, a pinned disc mill, a ball mill or a roll mill. In a further version of the present invention, the dried polymer can also be milled or ground by the combinations of two or more of the above-described mills.

In a preferred embodiment of the processes according to the invention, the water-absorbing polymers obtained are particles having an inner region and a surface region bordering the inner region. The surface region has a different chemical composition from the inner region, or differs from the inner region in a physical property. Physical properties in which the inner region differs from the surface region are, for example, the charge density or the degree of crosslinking.

These water-absorbing polymers having an inner region and a surface region bordering the inner region are preferably obtainable by post-crosslinking reactive groups close to the surface of the particles of the particulate hydrogel polymer (PC). This post-crosslinking can be effected thermally, photochemically or chemically.

Preferred post-crosslinkers are the compounds of crosslinker classes II and IV mentioned in connection with the crosslinkers (α3).

Among these compounds, particularly preferred post-crosslinkers are diethylene glycol, triethylene glycol, polyethylene glycol, glycerol, polyglycerol, propylene glycol, diethanolamine, triethanolamine, polyoxypropylene, oxyethylene-oxypropylene block copolymers, sorbitan fatty acid esters, polyoxyethylene sorbitan fatty acid esters, trimethylolpropane, pentaerythritol, polyvinyl alcohol, sorbitol, 1,3-dioxolan-2-one (ethylene carbonate), 4-methyl-1,3-dioxolan-2-one (propylene carbonate), 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one, 1,3-dioxolan-2-one, poly-1,3-dioxolan-2-one.

Particular preference is given to using ethylene carbonate as the post-crosslinker.

Preferred embodiments of the water-absorbing polymers are those which are post-cross-linked by crosslinkers of the following crosslinker classes or by crosslinkers of the following combinations of crosslinker classes: II, IV and II IV.

The post-crosslinker is preferably used in an amount within a range from 0.01 to 30% by weight, more preferably in an amount within a range from 0.1 to 20% by weight and further preferably in an amount within a range from 0.3 to 5% by weight, based in each case on the weight of the superabsorbent polymers in the post-crosslinking.

It is likewise preferred that the post-crosslinking is effected by contacting a solvent comprising preferably water, water-miscible organic solvents, for instance methanol or ethanol or mixtures of at least two thereof, and the post-crosslinker with the outer region of the hydrogel polymer particles. The hydrogel polymer particles are then typically heated to a temperature within a range from 30 to 300° C., more preferably within a range from 100 to 200° C. to complete the surface- or post-crosslinking reaction and remove excess water or other solvent used as a carrier. The contacting is preferably effected by spraying the mixture consisting of post-crosslinker and solvent onto the hydrogel polymer particles and then mixing the hydrogel polymer particles contacted with the mixture. The post-crosslinker is present in the mixture preferably in an amount within a range from 0.01 to 20% by weight, more preferably in an amount within a range from 0.1 to 10% by weight, based on the total weight of the mixture. It is additionally preferred that contact with the hydrogel polymer particles is effected in an amount within a range from 0.01 to 50% by weight, more preferably in an amount within a range from 0.1 to 30% by weight, based in each case on the weight of the hydrogel polymer particles.

Useful condensation reactions preferably include the formation of ester, amide, imide or urethane bonds, and preference being given to the formation of ester bonds.

The inventive hydrogel polymers and/or water-absorbing polymers can additionally be admixed with further additives including those that act as effect substances. Additives may be added to the water-absorbing polymer at any stage of the production process, including into the monomer, the wet gel or the dried polymer before or after post-crosslinking. If the additive is sensitive to heat, abrasion or other steps of the manufacturing process, it may be preferable to be added after the post-crosslinking step as one of the last production steps. Or it may be that ease of addition, or activity or desired effect of the additive is improved. Such additions after post-crosslinking are generally referred to as finishing or finishing treatments.

Preferred additives are additionally release agents, for instance inorganic or organic pulverulent release agents. These release agents are preferably used in amounts within a range from 0 to 2% by weight, more preferably within a range from 0.1 to 1.5% by weight, based on the weight of the hydrogel polymer and/or of the water-absorbing polymer. Preferred release agents are wood flour, pulp fibers, powdered bark, cellulose powder, mineral fillers such as perlite, synthetic fillers such as nylon powder, rayon powder, diatomaceous earth, bentonite, kaolin, zeolites, talc, loam, ash, carbon dust, magnesium silicates, fertilizers or mixtures of the substances. Finely divided fumed silica, as sold under the Aerosil trade name by Evonik Degussa, is preferred.

In a further preferred embodiment of the process according to the invention, the hydrogel polymer particles and/or the water-absorbing polymer particles are contacted with an effect substance additive, for example a polysugar, a polyphenolic compound, for example hydrolysable tannins or a compound containing silicon-oxygen, microbe inhibiting substances, enzyme inhibitors, odor absorbers, odor maskers, anti-perspirants and the like, or a mixture of at least two effect substances based thereon. The effect substance can be added either in solid form (powder) or in dissolved form with a solvent, the effect substance being added not earlier than after process step iii). In the context of the present invention, an effect substance additive is understood to mean a substance which serves for odor inhibition.

According to the invention, polysugars by which the person skilled in the art understands those from the group of the familiar starches and derivatives thereof, celluloses and derivatives thereof, cyclodextrins. Cyclodextrins are preferably understood to mean α-cyclodextrin, β-cyclodextrin, α-cyclodextrin or mixtures of these cyclodextrins.

Preferred compounds containing silicon-oxygen are zeolites. The zeolites used may be all synthetic or natural zeolites known to those skilled in the art. Preferred natural zeolites are zeolites from the natrolite group, the harmotone group, the mordenite group, the chabasite group, the faujasite group (sodalite group) or the analcite group. Examples of natural zeolites are analcime, leucite, pollucite, wairakite, bellbergite, bikitaite, boggsite, brewsterite, chabazite, willhendersonite, cowlesite, dachiardite, edingtonite, epistilbite, erionite, faujasite, ferrierite, amicite, garronite, gismondine, gobbinsite, gmelinite, gonnardite, goosecreekite, harmotome, phillipsite, wellsite, clinoptilolite, heulandite, laumontite, levyne, mazzite, merlinoite, montesommaite, mordenite, mesolite, natrolite, scolecite, offretite, paranatrolite, paulingite, perlialite, barrerite, stilbite, stellerite, thomsonite, tschernichite or yugawaralite. Preferred synthetic zeolites are zeolite A, zeolite X, zeolite Y, zeolite P, or the product ABSCENTS®.

The cations present in the zeolites used in the process according to the invention are preferably alkali metal cations such as $Li^+$, $Na^+$, $K^+$, $Rb^+$, $Cs^+$ or $Fr^+$ and/or alkaline earth metal cations such as $Mg^{2+}$, $Ca^{2+}$, $Sr^{2+}$ or $Ba^{2+}$.

The zeolites used may be zeolites of what is called the "intermediate" type, in which the $SiO_2/AlO_2$ ratio is less than 10; the $SiO_2/AlO_2$ ratio of these zeolites is more preferably within a range from 2 to 10. In addition to these "intermediate" zeolites, it is also possible to use zeolites of the "high" type, which include, for example, the known "molecular sieve" zeolites of the ZSM type, and beta-zeolite. These "high" zeolites are preferably characterized by an $SiO_2/AlO_2$ ratio of at least 35, more preferably by an $SiO_2/AlO_2$ ratio within a range from 200 to 500.

The zeolites are preferably used in the form of particles with a mean particle size within a range from 1 to 500 μm, more preferably within a range from 2 to 200 μm and further preferably within a range from 5 to 100 μm.

The effect substances are used in the processes according to the invention preferably in an amount within a range from 0.1 to 50% by weight, more preferably within a range from 1 to 40% by weight and further preferably in an amount within a range from 5 to 30% by weight, based in each case on the weight of the hydrogel polymer particles and/or water-absorbing polymer particles.

Preferred microbe-inhibiting substances are in principle all substances active against Gram-positive bacteria, for example 4-hydroxybenzoic acid and salts and esters thereof, N-(4-chlorophenyl)-N'-(3,4-dichlorophenyl)urea, 2,4,4'-trichloro-2'-hydroxydiphenyl ether (triclosan), 4-chloro-3,5-dimethylphenol, 2,2'-methylenebis(6-bromo-4-chlorophenol), 3-methyl-4-(1-methylethyl)phenol, 2-benzyl-4-chlorophenol, 3-(4-chlorophenoxy)-1,2-propanediol, 3-iodo-2-propynyl butylcarbamate, chlorhexidine, 3,4,4'-trichlorocarbonilide (TTC), antibacterial fragrances, thymol, thyme oil, eugenol, clove oil, menthol, mint oil, farnesol, phenoxyethanol, glyceryl monocaprate, glyceryl monocaprylate, glyceryl monolaurate (GML), diglyceryl monocaprate (DMC), N-alkylsalicylamides, for example N-n-octylsalicylamide or N-n-decylsalicylamide.

Suitable enzyme inhibitors are, for example, esterase inhibitors. These are preferably trialkyl citrates such as trimethyl citrate, tripropyl citrate, triisopropyl citrate, tributyl citrate and especially triethyl citrate (Hydagen TM CAT, Cognis GmbH, Düsseldorf, Germany). The substances inhibit enzyme activity and as a result reduce odor formation. Further substances useful as esterase inhibitors are sterol sulphates or phosphates, for example lanosterol sulphate or phosphate, cholesterol sulphate or phosphate, campesterol sulphate or phosphate, stigmasterol sulphate or phosphate and sitosterol sulphate or phosphate, dicarboxylic acids and esters thereof, for example glutaric acid, monoethyl glutarate, diethyl glutarate, adipic acid, monoethyl adipate, diethyl adipate, malonic acid and diethyl malonate, hydroxycarboxylic acids and esters thereof, for example citric acid, malic acid, tartaric acid or diethyl tartrate, and zinc glycinate.

Suitable odor absorbers are substances which can absorb and substantially retain odor-forming compounds. They lower the partial pressure of the individual components and thus also reduce the rate of spread thereof. It is important that perfumes must remain unimpaired. Odor absorbers generally have no effect against bacteria. They contain, for example, as the main constituent, a complex zinc salt of ricinoleic acid or specific, substantially odor-neutral fragrances known to the person skilled in the art as "fixatives", for example extracts of labdanum or *styrax* or particular abietic acid derivatives. The function of odor maskers is fulfilled by odorants or perfume oils which, in addition to their function as odor maskers, impart their particular fragrance note to the deodorants. Examples of perfume oils include mixtures of natural and synthetic odorants. Natural odorants are extracts of flowers, stems and leaves, fruits, fruit skins, roots, woods, herbs and grasses, needles and twigs, and also resins and balsams. Additionally useful are animal raw materials, for example civet and castoreum. Typical synthetic odorant compounds are products of the ester, ether, aldehyde, ketone, alcohol and hydrocarbon type. Odorant compounds of the ester type are, for example, benzyl acetate, p-tert-butylcyclohexyl acetate, linalyl acetate, phenylethyl acetate, linalyl benzoate, benzyl formate, allyl cyclohexylpropionate, styrallyl propionate and benzyl salicylate. The ethers include, for example, benzyl ethyl ether; the aldehydes include, for example, the linear alkanals having 8 to 18 carbon atoms, citral, citronellal, citronellyloxyacetaldehyde, cyclamen aldehyde, hydroxycitronellal, lilial and bourgeonal; the ketones include, for example, the ionones and methyl cedryl ketone; the alcohols include anethole, citronellol, eugenol, isoeugenol, geraniol, linalool, phenylethyl alcohol and terpineol; the hydrocarbons include principally the terpenes and balsams. Preference is given, however, to using mixtures of different odorants which together produce a pleasing fragrance note. Suitable perfume oils are also essential oils of relatively low volatility which are usually used as aroma components, for example sage oil, camomile oil, clove oil, melissa oil, mint oil, cinnamon leaf oil, lime blossom oil, juniperberry oil, vetiver oil, olibanum oil, galbanum oil, labdanum oil and lavender oil. Preference is given to using bergamot oil, dihydromyrcenol, lilial, lyral, citronellol, phenylethyl alcohol, alpha-hexylcinnamaldehyde, geraniol, benzylacetone, cyclamen aldehyde, linalool, Boisambrene Forte, ambroxan, indole, Hedione, Sandelice, lemon oil, mandarin oil, orange oil, allyl amyl glycolate, cyclovertal, lavender oil, clary sage oil, beta-damascone, geranium oil bourbon, cyclohexyl salicylate, Vertofix Coeur, Iso-E-Super, Fixolide NP, Evernyl, iraldein gamma, phenylacetic acid, geranyl acetate, benzyl acetate, rose oxide, Romilat, Irotyl and Floramat, alone or in mixtures.

Antiperspirants reduce the formation of perspiration by influencing the activity of the eccrine sweat glands, and thus counteract underarm wetness and body odor. Suitable astringent active antiperspirant ingredients are in particular salts of aluminum, zirconium or zinc. Such suitable antihydrotically active ingredients are, for example, aluminum chloride, aluminum chlorohydrate, aluminum dichlorohydrate, aluminum sesquichlorohydrate and the complexes thereof, for example with propylene 1,2-glycol, aluminum hydroxyallantoinate, aluminum chloride tartrate, aluminum zirconium trichlorohydrate, aluminum zirconium tetrachlorohydrate, aluminum zirconium pentachlorohydrate and the complexes thereof, for example with amino acids such as glycine.

Examples of further additives in the context of the present invention include anticaking compounds, for example kaolin, Aerosils®, Sipernats®, and the like, insoluble inorganic additives based on silicon, for example silicas or silica sols, aluminum salts such as aluminum sulphate or aluminum lactate, surfactants, viscosity modifiers or the like, which are applied to the surface of the polymer particles or else react with the free polymer chains of the polymer particle.

Suitable apparatus for mixing or spraying is any which allows homogeneous distribution of a solution, powder, suspension or dispersion on or with the hydrogel polymer particles ( ) or water-absorbing polymers. Examples are Lödige mixers (manufactured by Gebrüder Lödige Maschinenbau GmbH), Gericke multi-flux mixers (manufactured by Gericke GmbH), DRAIS mixers (manufactured by DRAIS GmbH Spezialmaschinenfabrik Mannheim), Hosokawa mixers (Hosokawa Mokron Co., Ltd.), Ruberg mixers (manufactured by Gebr. Ruberg GmbH & Co. KG Nieheim), Huttlin coaters (manufactured by BWI Hiittlin GmbH Steinen), fluidized bed driers or spray granulators from AMMAG (manufactured by AMMAG Gunskirchen, Austria) or Heinen (manufactured by A. Heinen AG Anlagenbau Varel), Patterson-Kelly mixers, NARA paddle mixers, screw mixers, pan mixers, fluidized bed driers or Schugi mixers. For contacting in a fluidized bed, it is possible to employ all fluidized bed processes which are known to those skilled in the art and appear to be suitable. For example, it is possible to use a fluidized bed coater.

A further contribution to the solution of the problem stated at the outset is made by the process for preparing a water-absorbing polymer, comprising the process steps of
(i) mixing
($\alpha$1) 0.1 to 99.999% by weight, preferably 20 to 98.99% by weight and more preferably 30 to 98.95% by weight of polymerizable, ethylenically unsaturated monomers containing acid groups, or salts thereof, or polymerizable, ethylenically unsaturated monomers including a protonated or quaternized nitrogen, or mixtures thereof, particular preference being given to mixtures including at least ethylenically unsaturated monomers containing acid groups, preferably acrylic acid,
($\alpha$2) 0 to 70% by weight, preferably 1 to 60% by weight and more preferably 1 to 40% by weight of polymerizable, ethylenically unsaturated monomers copolymerizable with ($\alpha$1),
($\alpha$3) 0.001 to 10% by weight, preferably 0.01 to 7% by weight and more preferably 0.05 to 5% by weight of one or more crosslinkers,
($\alpha$4) 0 to 30% by weight, preferably 1 to 20% by weight and more preferably 5 to 10% by weight of water-soluble polymers,
($\alpha$5) 0-90% by weight, preferably 2.5-75% by weight and more preferably 10-60% by weight of water, and
($\alpha$6) 0-20% by weight, preferably 0-10% by weight and more preferably 0.1-8% by weight of one or more additives, where the sum of the weights of ($\alpha$1) to ($\alpha$6) is 100% by weight,
(ii) free-radical polymerization with crosslinking to form a water-insoluble, aqueous untreated hydrogel polymer,
(iii) comminuting the hydrogel polymer,
(iv) drying the hydrogel polymer,
(v) grinding and sieving the hydrogel polymer to size,
(vi) surface post-crosslinking the ground and sieved hydrogel polymer and
(vii) finishing the water-absorbing polymer,
wherein
the water-absorbing polymer has been treated with 0.0001 to 3% by weight, preferably 0.002 to 2% by weight and more preferably 0.007 to 1.8% by weight of a peroxo compound, based on the acrylic acid, after the polymerization, are added in steps (iii) to (vii).

In a further preferred embodiment, the peroxo compound is used in an amount of 0.0001 to 1.5% by weight, based on the acrylic acid, after the polymerization.

In a further embodiment, in accordance with the invention, the peroxo compound is selected those from the group of organic and inorganic peroxo compounds.

In a further preferred embodiment, in accordance with the invention, an alkali metal salt of an inorganic peroxo compound is used.

In a further embodiment, in accordance with the invention, the peroxo compound is added in steps (iii) to (vii), explicitly in step (iii), (iv), (v), (vi) and/or (vii).

In a further particularly preferred embodiment, in accordance with the invention, the peroxo compound is added in step (vii).

In one further embodiment the process for preparing a water-absorbing polymer comprises the process steps of
(i) mixing
($\alpha$1) 0.1 to 99.999% by weight, preferably 20 to 98.99% by weight and more preferably 30 to 98.95% by weight of polymerizable, ethylenically unsaturated monomers containing acid groups, or salts thereof, or polymerizable, ethylenically unsaturated monomers including a protonated or quaternized nitrogen, or mixtures thereof, particular preference being given to mixtures including at least ethylenically unsaturated monomers containing acid groups, preferably acrylic acid,
($\alpha$2) 0 to 70% by weight, preferably 1 to 60% by weight and more preferably 1 to 40% by weight of polymerizable, ethylenically unsaturated monomers copolymerizable with ($\alpha$1), (α3) 0.001 to 10% by weight, preferably 0.01 to 7% by weight and more preferably 0.05 to 5% by weight of one or more crosslinkers, (α4) 0 to 30% by weight, preferably 1 to 20% by weight and more preferably 5 to 10% by weight of water-soluble polymers, (α5) 0-90% by weight, preferably 2.5-75% by weight and more preferably 10-60% by weight of water, and (α6) 0-20% by weight, preferably 0-10% by weight and more preferably 0.1-8% by weight of one or more additives, where the sum of the weights of (α1) to (α6) is 100% by weight, (ii) free-radical polymerization with crosslinking to form a water-insoluble, aqueous untreated hydrogel polymer, (iii) comminuting the hydrogel polymer, (iv) drying the hydrogel polymer, (v) grinding and sieving the hydrogel polymer to size, (vi) surface post-crosslinking the ground and sieved hydrogel polymer and (vii) drying and finishing the water-absorbing polymer, wherein the water-absorbing polymer has been treated with 0.0001 to 3% by weight, preferably 0.002 to 2% by weight and more preferably 0.007 to 1.8% by weight of a peroxo compound, based on the acrylic acid, after the polymerization, are added in steps (iii) to (vii).

The improved odor control of the water-absorbing polymer of the present invention is shown in the following examples, and tests, directed to the prevention of the formation of ammonia as determined by the Determination of Ammonia ($NH_3$) release (*Proteus mirabilis*) Test, and the reduction of organic molecules as determined by the Determination of the Reduction in Organic Molecule Odor Test. SAP give some prevention of the formation of ammonia. In particular, the following reference SAP sample shows 6-7 hrin the prevention of the formation of ammonia. In accordance with the present invention, the prevention of the formation of ammonia in accordance with the Determination of Ammonia ($NH_3$) release (*Proteus mirabilis*) Test is more than 8 hours, or ranges from 12 to 35 hr, or ranges from 15 to 30 hr, or from 17 to 25 hr. or from 18 to 22 hr; and the reduction of organic molecules has been reduced based on the molecule. As shown in the reference sample, the % reduction after 16 hr. in the organic molecules including pyrrole, furfuryl mercaptan, (S)-(+)-carvone, indole, trimethylamine, and dimethyl disulfide is 0%. In accordance with the present invention, the % reduction in organic molecules in accordance with the Determination of the Reduction in Organic Molecule Odor Test are as follows:

a % reduction ranging from 50 to 99.9%, or from 60 to 99.9%, or from 70 to 99.9%, or from 80 to 99.9%, or from 90 to 99.9%, or from 95 to 99.8%, of pyrrole; and/or a % reduction ranging from 50 to 99.9%, or from 60 to 99.9%, or from 70 to 99.9%, or from 80 to 99.9%, or from 90 to 99.9%, or from 95 to 99.8%, of furfuryl mercaptan; and/or a % reduction ranging from 50 to 99.9%, or from 60 to 99.9%, or from 70 to 99.9%, or from 80 to 99.9%, or from 90 to 99.9%, or from 95 to 99.8%, of (S)-(+)-carvone; and/or a % reduction ranging from 50 to 99.9%, or from 60 to 99.9%, or from 70 to 99.9%, or from 80 to 99.9%, or from 90 to 99.9%, or from 95 to 99.8%, of indole; and/or a % reduction ranging from 10 to 30%, or from 15 to 27%, of trimethylamine; and/or a % reduction ranging from 50 to 99.9%, or from 60 to 99.9%, or from 70 to 99.9%, or from 80 to 99.9%, or from 85 to 96%, of dimethyl disulfide.

As shown above and in the following examples, the present invention provides a superabsorbent polymer including a single odor controltreatment, wherein the resulting superabsorbent polymer has superior ammonia odor control and reduces not just control one type of organic molecule odor, but a wide variety of types of organic molecule odors that usually require different treatments.

A further contribution to the solution of the problems described at the outset is made by a composite including the inventive water-absorbing polymers or the hydrogel polymers, or the water-absorbing polymers or hydrogel polymers obtainable by the processes according to the invention, and a substrate. It is preferable that the inventive water-absorbing polymers or hydrogel polymers and the substrate are bonded in a fixed manner to one another. Preferred substrates are films of polymers, for example of polyethylene, polypropylene or polyamide, metals, nonwovens, fluff, tissues, fabrics, natural or synthetic fibers, or foams. It is additionally preferred in accordance with the invention that the composite comprises at least one region which includes water-absorbing polymers or hydrogel polymers in an amount in the range from about 15 to 100% by weight, preferably about 30 to 100% by weight, more preferably from about 50 to 99.99% by weight, further preferably from about 60 to 99.99% by weight and even further preferably from about 70 to 99% by weight, based in each case on the total weight of the region of the composite in question, this region preferably having a size of at least 0.01 $cm^3$, preferably at least 0.1 $cm^3$ and most preferably at least 0.5 $cm^3$.

A further contribution to the solution of at least one of the problems stated at the outset is made by a process for producing a composite, wherein the inventive water-absorbing polymers or the superabsorbents obtainable by the process according to the invention and a substrate and optionally an additive are contacted with one another. The substrates used are preferably those substrates which have already been mentioned above in connection with the inventive composite.

A contribution to the solution of at least one of the problems stated at the outset is also made by a composite obtainable by the process described above, this composite preferably having the same properties as the above-described inventive composite.

A further contribution to the solution of at least one of the problems stated at the outset is made by chemical products including the inventive water-absorbing polymers or hydrogel polymers or an inventive composite. Preferred chemical products are especially foams, moldings, fibers, foils, films, cables, sealing materials, liquid-absorbing hygiene articles, especially diapers, nappies and sanitary towels, carriers for plant growth or fungal growth regulators or plant protection active ingredients, additives for building materials, packaging materials or soil additives.

The use of the inventive water-absorbing polymers or of the inventive composite in chemical products, preferably in the aforementioned chemical products, especially in hygiene articles such as nappies or sanitary towels, and the use of the water-absorbing polymer particles as carriers for plant growth or fungal growth regulators or plant protection active ingredients also make a contribution to the achievement of at least one of the problems stated at the outset. In the case of use as a carrier for plant growth or fungal growth regulators or plant protection active ingredients, it is preferred that the plant growth or fungal growth regulators or plant protection active ingredients can be released over a period controlled by the carrier.

Test Methods

Unless stated otherwise hereinafter, the measurements conducted herein are according to ERT methods. "ERT" stands for EDANA Recommended Test and "EDANA" for European Disposables and Nonwovens Association. All test methods are in principle, unless stated otherwise, conducted at an ambient temperature of 23±2° C. and a relative air humidity of 50±10%.

Particle Size Distribution (PSD)

The particle size distribution of the water-absorbing polymer particles is determined analogously to EDANA recommended test method No. WSP 220.3-10 "Particle Size Distribution.".

Centrifuge Retention Capacity (CRC).

The centrifuge retention capacity was determined by EDANA (European Disposables and Nonwovens Association) recommended test method No. WSP 241.3-10, "Centrifuge retention capacity".

Absorption Against a Pressure of 0.7 Psi (AAP)

The absorption under pressure was determined as the AAP (Absorption Against Pressure) to WSP 242.3-10 on the overall particle fraction. Accordingly, 0.90 g of the test substance (sieved off between 150 and 850 μm) was weighed into a test cylinder of internal diameter 60.0 mm with a sieve base (400 mesh) (concentration: 0.032 g/cm$^2$) and distributed homogeneously. A cylindrical weight (50 g/cm$^2$=0.7 psi) with an external diameter of 59.2 mm was placed onto the test substance. Filter plates were placed into a plastic dish, and were covered with a filter paper. The plastic dish was filled with 0.9% NaCl solution until the liquid level concluded with the upper edge of the filter plates. Subsequently, the prepared test units were placed onto the filter plates. After a swelling time of 60 minutes, the test units were withdrawn and the weight was removed. The amount of liquid absorbed was determined gravimetrically and converted to the amount absorbed per 1 gram of test substance.

Determination of Ammonia ($NH_3$) Release (*Proteus mirabilis*):

*Proteus mirabilis* was grown on a slanted Caso agar at 37° C. overnight. The bacteria culture was washed off with 5 ml of synthetic urine (25 g/l urea, 9 g/l sodium chloride, 5 g/l glucose, 4 g/l potassium sulphate, 2.5 g/l ammonium sulphate, 0.7 g/l calcium acetate, 0.7 g/l magnesium sulphate×7 $H_2O$, 0.5 g/l yeast extract, 5 g/l meat extract, 5 g/l peptone). The microbe count of the synthetic urine was adjusted such that an initial microbe count of about $10^5$ CFU/ml urine was present. In each case 33 ml of the synthetic urine with added bacteria were transferred into Erlenmeyer flasks, and 1 g of superabsorbent was added. The vessels were closed with a rubber stopper, through the hole of which was passed a Dräger diffusion tube (ammonia 20/a-D), and incubated at 37° C. in an incubator. The ammonia released was measured in ppm×h.

Determination of the Reduction in Organic Molecule Odor

By Solid Phase Microextration (SPME)—Gas Chromatography (GC)

This test determines the odor reduction of six different organic malodors, representing six different classes of chemical compounds.

0.50 g of the superabsorbent to be determined are weighed accurately into a 200 ml Erlenmeyer flask and admixed with 11.0 g of a mixture consisting of 100 ng/ml dimethyl trisulphide, 0.5 ng/ml pyrrole, 50 ng/ml furfuryl mercaptan, 0.5 ng/ml (S)-(+)-carvone, 0.5 ng/ml indole and 13 000 ng/ml trimethylamine in a 0.9% by weight aqueous NaCl solution. The flask is sealed with a threaded adapter having a septum and stored in a climate-controlled cabinet at 37° C. for 16 h to establish equilibrium in the vapour space. Now the SPME phase is introduced into the vapor space for 30 min and then injected directly into a gas chromatograph, for desorption and malodor amount analysis. The decrease or the reduction in concentration of the odorant is determined in relation to the corresponding reference sample in %.

Instrument Parameters:

Flask 200 ml Erlenmeyer flask with NS 29=volume 255 ml with threaded adapter and septum
SPME Phase: Supelco Carboxen/PDMS-black
GC column RESTEK Corp. RTX-50, 30 m, 0.53
GC Hewlett Packard 5890
Carrier Gas: He
Heating rates:

| 7 min. | | 30° C. |
|---|---|---|
| 10° C./min. | to | 180° C. |
| 30° C./min. | to | 250° C. |

EXAMPLES

The examples which follow serve for further illustration of the invention, but without restricting it thereto.

For the inventive examples which follow, a defined particle size distribution (PSD) was used (150 μm to 850 μm).

The term "SX" as used in the description is understood to mean the thermal surface post-crosslinking of the precursor (PC). The precursor corresponds to the hydrogel polymer obtained after the first drying and milling, with the aforementioned particle distribution.

Description of the Production of the SAP Samples
Polymer Material (Powder A)

A monomer solution consisting of 300 g of acrylic acid, neutralized to an extent of 60 mol % with 200.2 g of 50% NaOH, 474.8 g of water, 1.62 g of polyethylene glycol-300 diacrylate, 0.89 g of monoallyl polyethylene glycol-450 monoacrylate was freed of the dissolved oxygen by degassing with nitrogen and cooled to the start temperature of about 4° C. After the start temperature had been attained, the initiator solution consisting of 0.3 g of sodium peroxodisulphate in 10 g of water, 0.07 g of 35% hydrogen peroxide solution in 10 g of water and 0.015 g of ascorbic acid in 2 g of water was added. An exothermic polymerization reaction took place. The adiabatic end temperature was about 100° C. The hydrogel formed was comminuted with a laboratory meat grinder (5 mm die plate) and the comminuted sample was dried at 170° C. for 90 minutes in a laboratory air circulation drying cabinet. The dried polymer was first coarsely crushed and then ground by means of an SM100 cutting mill having an aperture size of 2 mm, and sieved to a powder having a particle size of 150 to 850 μm. 100 g of the powder were coated with a solution of 1.0 g of ethylene carbonate and 3.0 g of deionized water. This was done by applying the solution with a syringe (0.45 mm cannula) to the polymer powder present in the mixer. The coated powder was then heated in a drying cabinet at 170° C. over a period of 90 minutes.

Example 1, Reference Sample

The reference sample used was powder A without further additional treatment.

Example 2

100 g of powder A were admixed with 0.5 g of potassium peroxomonosulphate triple salt (Caro's acid) and homogenized on an overhead agitator for about 2 h.

Example 3

100 g of powder A were admixed with 1.0 g of potassium peroxomonosulphate triple salt and homogenized on an overhead agitator for about 2 h.

Ammonia Odor Control:

| Sample Reference | Retention [g/g] | AAP 0.7 psi [g/g] | NH₃ odor control [hr] |
|---|---|---|---|
| Reference sample, Example 1 | 30.2 | 21.2 | 6-7 |
| Example 2 | 31.0 | 20.4 | 18-20 |
| Example 3 | 31.2 | 20.3 | 20-22 |

As can be seen by the above results, the inventive odor-control superabsorbent polymer is surprisingly effective in preventing the formation of ammonia for 18 to 22 hours, while maintaining excellent absorption properties compared to the reference example where ammonia is generated after only 6 or 7 hours.

Organic Molecules—Odor Control:

| Sample Reference | Reduction in pyrrole [%] compared to reference after 16 hr | Reduction in furfuryl mercaptan [%] compared to reference after 16 hr | Reduction in (S)-(+)-carvone [%] compared to reference after 16 hr |
|---|---|---|---|
| Reference sample, example 1 | 0 | 0 | 0 |
| Inventive Example 2 | 99.2 | 95.5 | 97.9 |
| Inventive Example 3 | 99.2 | 96.7 | 97.5 |

| Sample Reference | Reduction in indole [%] compared to reference after 16 hr | Reduction in trimethylamine [%] compared to reference after 16 hr | Reduction in dimethyl disulfide [%] compared to reference after 16 hr |
|---|---|---|---|
| Reference sample, example 1 | 0 | 0 | 0 |
| Inventive Example 2 | 95.2 | 18.3 | 93.9 |
| Inventive Example 3 | 98.8 | 23.9 | 89.3 |

As clearly demonstrated by the above results, the inventive odor-control superabsorbent is effective in controlling malodors not only from ammonia, but also those from organic molecules. The malordous organic substances used: pyrrole, furfuryl mercaptan, (S)-(+)-carvone, indole, trimethylamine and dimethyl disulfilde are six different well known malodors, representing six different chemical classes of compounds. The inventive absorbents surprisingly are capable of eliminating up to 99% of these odors in the headspace above the absorbent.

Examples 2 and 3 were repeated with equivalent amounts of different salts of peroxomonosulphate and peroxodisulphate and sulpho monoperacid. All peroxo compounds tested showed excellent properties in controlling malodors and achieved similar results as the once listed in the tables above.

Additionally the peroxo compound potassium peroxomonosulphate triple salt was tested with various different SAP samples supplemental to the above tests with powder A. All tested SAP particles based on monomers in different concentrations, different internal crosslinkers, different post-crosslinkers, and different production conditions which were treated according to Example 2 or Example 3 showed outstanding results in preventing the formation of ammonia for 18 to 22 hours and in controlling malodors not only from ammonia, but also those from organic molecules.

The invention claimed is:

1. A water-absorbing polymer comprising:
   ($\alpha$1) 20-99.999% by weight of polymerized, ethylenically unsaturated monomers bearing acid groups, or salts of polymerized, ethylenically unsaturated monomers bearing acid groups, or polymerized, ethylenically unsaturated monomers comprising a protonated nitrogen, polymerized, ethylenically unsaturated monomers comprising a quaternized nitrogen, or mixtures thereof,
   ($\alpha$2) 0-79.999% by weight of polymerized monoethylenically unsaturated monomers copolymerizable with ($\alpha$1),
   ($\alpha$3) 0.001-5% by weight of one or more crosslinkers,
   ($\alpha$4) 0-30% by weight of a water-soluble polymer,
   ($\alpha$5) 0-20% by weight of water, and
   ($\alpha$6) 0-20% by weight of one or more additives, where the sum of the weights of the recited compounds in ($\alpha$1) to ($\alpha$6) is 100% by weight,
   wherein the water-absorbing polymer has been treated with 0.0001 to 3% by weight of a potassium peroxomonosulfate triple salt, based on ($\alpha$1), after the polymerization.

2. The water-absorbing polymer according to claim 1, wherein the water-absorbing polymer has been treated with 0.0001 to 1.5% by weight of the potassium peroxomonosulfate triple salt, based on ($\alpha$1), after the polymerization.

3. A composite including a water-absorbing polymer according to claim 1.

4. The water-absorbing polymer according to claim 1, wherein the water-absorbing polymer has a prevention of the formation of ammonia in accordance with the Determination of Ammonia (NH₃) release (*Proteus mirabilis*) Test of from 15 to 30 hr.

5. The water-absorbing polymer according to claim 1, wherein the water-absorbing polymer has a % reduction ranging from 50 to 99.9%, of pyrrole; or
   a % reduction ranging from 50 to 99.9%, of furfuryl mercaptan; or
   a % reduction ranging from 50 to 99.9% of (S)-(+)-carvone; or
   a % reduction ranging from 50 to 99.9% of indole; or
   a % reduction ranging from 10 to 30% of trimethylamine; or
   a % reduction ranging from 50 to 99.9% of dimethyl disulfide in accordance with the Determination of the Reduction in Organic Molecule Odor Test.

* * * * *